(12) United States Patent
Mastio (10) Patent No.: US 10,155,679 B2
(45) Date of Patent: Dec. 18, 2018

(54) SALT WATER POOL CHLORINATOR HAVING A SENSOR

(71) Applicant: ZODIAC GROUP AUSTRALIA PTY LTD, Smithfield, New South Wales (AU)

(72) Inventor: Emmanuel Mastio, Frenchs Forest (AU)

(73) Assignee: Zodiac Group Australia Pty Limited, Smithfield, New South Wales (AU)

( * ) Notice: Subject to any disclaimer, the term of this patent is extended or adjusted under 35 U.S.C. 154(b) by 924 days.

(21) Appl. No.: 14/335,996

(22) Filed: Jul. 21, 2014

(65) Prior Publication Data

US 2014/0326680 A1 Nov. 6, 2014

Related U.S. Application Data

(63) Continuation of application No. PCT/AU2013/000076, filed on Jan. 29, 2013.
(Continued)

(30) Foreign Application Priority Data

Jan. 27, 2012 (AU) ............... 2012900326

(51) Int. Cl.
*C02F 1/46* (2006.01)
*C02F 1/467* (2006.01)
(Continued)

(52) U.S. Cl.
CPC ........ *C02F 1/4674* (2013.01); *C02F 1/46104* (2013.01); *C25B 1/26* (2013.01);
(Continued)

(58) Field of Classification Search
CPC ................ C02F 1/4674; C02F 1/46104; C02F 2307/00; C02F 2305/02; C02F 2201/461;
(Continued)

(56) References Cited

U.S. PATENT DOCUMENTS 4,085,028 A * 4/1978 McCallum .......... C02F 1/46109
204/268
4,250,126 A 2/1981 Yates
(Continued)

FOREIGN PATENT DOCUMENTS

WO 2011032212 A1 3/2011
WO 2013110144 A1 8/2013

OTHER PUBLICATIONS

International Search Report dated Mar. 14, 2013 in Application No. PCT/US2013/000076.
(Continued)

*Primary Examiner* — Walter D. Griffin
*Assistant Examiner* — Cameron J Allen
(74) *Attorney, Agent, or Firm* — Kilpatrick Townsend & Stockton LLP; Dean W. Russell; Renae Bailey Wainwright (57) ABSTRACT

Disclosed herein is a unit for a salt water pool chlorinator that is arranged for water to flow therethrough. The unit is configured for an electrode assembly to be received therein and is arranged such that some of the water flows through the electrode assembly. The unit has a channel, defined by a barrier impermeable to water, arranged for some other of the water to flow through the channel. At least one port may be arranged at the channel whereby at least one of a sensor, a feeder and an extractor can use the port to respectively detect, feed into and extract water in the channel.

20 Claims, 12 Drawing Sheets

Related U.S. Application Data (60) Provisional application No. 61/625,129, filed on Apr. 17, 2012.

(51) Int. Cl.

| | | |
|---|---|---|
| *C25B 1/26* | (2006.01) | |
| *C25B 9/00* | (2006.01) | |
| *C02F 1/461* | (2006.01) | |
| *G01N 27/416* | (2006.01) | |
| *C02F 103/08* | (2006.01) | |
| *C02F 103/42* | (2006.01) | |

(52) U.S. Cl.
CPC ............ *C25B 9/00* (2013.01); *C02F 2103/08* (2013.01); *C02F 2103/42* (2013.01); *C02F 2201/004* (2013.01); *C02F 2201/461* (2013.01); *C02F 2209/04* (2013.01); *C02F 2209/05* (2013.01); *C02F 2209/055* (2013.01); *C02F 2209/06* (2013.01); *C02F 2209/07* (2013.01); *C02F 2209/15* (2013.01); *C02F 2209/18* (2013.01); *C02F 2209/29* (2013.01); *C02F 2305/02* (2013.01); *C02F 2307/00* (2013.01); *G01N 27/4168* (2013.01)

(58) Field of Classification Search
CPC .............. C02F 2103/08; C02F 2103/42; C02F 2201/004; C02F 2209/04; C02F 2209/05; C02F 2209/055; C02F 2209/06; C02F 2209/07; C02F 2209/15; C02F 2209/18; C02F 2209/29; C25B 1/26; C25B 9/00; G01N 27/4168
See application file for complete search history.

(56) References Cited

U.S. PATENT DOCUMENTS

| | | | |
|---|---|---|---|
| 4,472,256 A | 9/1984 | Hilbig | |
| 4,861,451 A | 8/1989 | David | |
| 5,037,519 A | 8/1991 | Wiscombe | |
| 5,062,940 A | 11/1991 | Davies | |
| 5,460,706 A | 10/1995 | Lisboa | |
| 6,007,693 A | 12/1999 | Silveri | |
| 6,096,202 A | 8/2000 | Fulmer | |
| 6,391,167 B1 | 5/2002 | Grannersberger | |
| 7,879,208 B2* | 2/2011 | Wu | C25B 9/08 204/278.5 |
| 8,603,331 B1* | 12/2013 | Koble | C02F 1/4674 204/194 |
| 8,920,615 B2 | 12/2014 | Davidson et al. | |
| 2006/0249400 A1 | 11/2006 | Bremauer | |
| 2007/0181439 A1 | 8/2007 | Wu et al. | |
| 2010/0250449 A1* | 9/2010 | Doyle | C02F 1/4674 705/302 |
| 2010/0313964 A1* | 12/2010 | Hin | C02F 1/006 137/15.01 |
| 2011/0180395 A1 | 7/2011 | Tucker | |
| 2011/0278158 A1* | 11/2011 | Briggs | C02F 1/4674 204/227 |
| 2013/0105403 A1* | 5/2013 | Chen | E04H 4/1281 210/739 |

OTHER PUBLICATIONS

International-Type Search Report dated Jun. 20, 2012 issued in AU2012900326.
International Search Report and Written Opinion for PCT Application No. PCT/US2015/011761, dated May 4, 2015, 14 pages.
International Preliminary Report on Patentability for PCT Application No. PCT/US2015/011761, dated Jul. 28, 2016, 11 pages.
Non Final Office Action for U.S. Appl. No. 14/598,742, dated Apr. 20, 2017, 6 pages.
Notice of Allowance for U.S. Appl. No. 14/598,742, dated Sep. 28, 2017, 5 pages.
Corrected Notice of Allowability for U.S. Appl. No. 14/598,742, dated Oct. 11, 2017, 2 pages.

* cited by examiner

SALT WATER POOL CHLORINATOR HAVING A SENSOR

CROSS-REFERENCE TO RELATED APPLICATIONS

This application is a continuation of International Application No. PCT/AU2013/000076 filed on Jan. 29, 2013 published in English on Aug. 1, 2013 as International Publication No. WO 2013/110144 A1, which application claims the benefit of Australian Patent Application No. 2012900326 filed on Jan. 27, 2012 and U.S. Provisional Patent Application No. 61/625,129 filed on Apr. 17, 2012, the contents of all of which are incorporated by this reference.

TECHNICAL FIELD

The present disclosure generally relates to a salt water pool chlorinator having a sensor. The sensor finds application specifically, though not exclusively, to salt water pool chlorination. The salt water pool chlorinator may be in the form of a unit and may additionally have a feeder or extractor.

BACKGROUND

Salt water pool chlorination involves electrolysis of at least one of sodium chloride and sodium bromide ("salt") dissolved in pool water to produce sanitizing agents such as hypochlorous acid and sodium hypochlorite. The electrolysis is achieved by passing a current through adjacent conductive plates immersed in the pool water.

Optimal operation of a salt water chlorinator can require the concentration of dissolved salts in the pool water be in the range of 1,800 and 6,000 parts per million, and that a concentration of stabilizers, such as cyanuric acid, when present are at appropriate levels. The pH of the pool water may also need to be maintained at an appropriate level.

In order to determine the concentration of chemicals in a pool, a person may employ so-called "test strips" or fill a container with a sample of pool water and subsequently test the water in the container.

U.S. Pat. No. 7,879,208 discloses a multi-port chlorine generator comprising sensors, located in one of the ports, for monitoring water parameters.

The above references to the background art do not constitute an admission that the art forms part of the common general knowledge of a person of ordinary skill in the art. The above references are also not intended to limit the application of the unit and method disclosed herein.

SUMMARY OF THE DISCLOSURE

In a first aspect there is disclosed a unit for a salt water pool chlorinator. The unit is arranged for water to flow through the unit. The unit is configured for an electrode assembly to be received therein and is arranged such that some of the water flows through the electrode assembly. The unit has a channel, defined by a barrier impermeable to water, arranged for some other of the water to flow through the channel. At least one port is arranged at the channel whereby at least one of a sensor, a feeder and/or an extractor is able to use the port to respectively detect, feed into and/or extract water in the channel.

By providing in the unit a separate water flow through the channel (i.e. separate to the water that flows through the electrode assembly), electrolysis can occur independently of sensing, feeding and/or extracting. Such an arrangement may, for example, allow a sensor in the channel to detect parameters that have not been altered by electrolysis. This is in contrast to U.S. Pat. No. 7,879,208, wherein the electrodes are configured to be in-line with the sensors. Furthermore, the sensors in U.S. Pat. No. 7,879,208 are not located in a channel that is separate to the electrodes, let alone in a channel that is defined by a barrier that is impermeable to water. Therefore, in U.S. Pat. No. 7,879,208 the detecting of parameters and the electrolysis are not performed on separate water flows.

The at least one port can be configured such that a sensor may be arranged to determine a concentration of a dissolved salt in the water when so flowing through the channel. Although, the sensor may alternatively be configured to measure any of: acidity; alkalinity; total alkalinity; biguanide; bromine; free bromine; chloride; chlorine; free chlorine; free and combined chlorine; conductivity; copper; cyanuric acid; hardness; calcium hardness; total hardness; hydrogen peroxide; iron; manganese; mineral/salt; monopersulfate; NaCl (salt); nitrate; oxidation reduction potential (ORP); ozone; pH; phosphate; quaternary ammonium compounds (QAC); and generally any chemical present in the water. Further, a number of sensors may be provided in one or more ports, with each sensor being configured to measure any of the above mentioned parameters.

The sensor may make it unnecessary for a person to manually take a sample of the water and subsequently measure the sample at a location remote from the pool. The measurement may not require a person. The measurement may be continuously or regularly initiated by a processor. The processor may cause a chemical for a pool, to be introduced through the feeder. The processor may control the injection of the chemical through the feeder in response to a concentration determined by the sensor. Examples of chemicals for a pool include but are not limited to: sodium bicarbonate; sodium carbonate; sodium bisulphate; sodium hypochlorite; chlorine; hydroxyethylidene diphosphonic acid complex; calcium chloride; hydrochloric acid; trichloroisocyanuric acid; sodium tetraborate pentahydrate; cyanuric acid; copper sulphate pentahydrate; boric acid; sodium dichloroisocyanurate dihydrate; calcium hypochlorite; potassium peroxymonopersulphate; aluminium sulphate; natural clarifier; cationic polyecrolyte; aluminium chlorhydrate; aluminium oxide; poly[oxyethylene(dimethyliminio) ethylene-(dimethyliminio)ethylene dichloride]; cupric ammonium complex; benzalkonium chloride; copper—triethanolamine complex (as copper); quaternary ammonium chloride; isocyanuric acid; sodium metabisulphite; 1-hydroxyethylidene-1,1-diphophonic acid; citric acid monohydrate; oxalic acid; magnesium sulphate heptahydrate; and aluminosilicate.

In one embodiment, the unit may further comprise an electrode assembly receptacle. The electrode assembly receptacle may be arranged for the electrode assembly to be received therein, with the receptacle as a whole being received in the unit. In embodiments where the electrode assembly receptacle is not present in the unit, the unit itself may be considered to be the electrode assembly receptacle.

While a barrier, or partition, may be provided to define the channel, it may not be necessary to have a dedicated barrier, or partition, within the unit to define the channel. In lieu of a dedicated barrier, the channel may at least partially be defined by a wall of the electrode assembly, when received in the unit, or a wall of the electrode assembly receptacle when present in the unit. Alternatively, the channel may be defined by both a wall of the electrode assembly and a wall of the electrode assembly receptacle. In a further embodiment the channel may be defined by a surface or surfaces of only one of the electrode assembly, electrode assembly receptacle or unit, or it may be defined by any combination of surfaces of these components. Such an arrangement may simplify the structure and manufacture of the unit.

The electrode assembly, or the electrode assembly receptacle with the electrode assembly arranged therein, may be easily removed from the unit (when worn out, for example), rather than removing the entire unit. This may reduce or eliminate the need for skilled labour (by an electrician or plumber for example), when replacing a worn out electrode assembly.

In an embodiment, the unit may have an inlet for water to enter into the unit and an outlet for water to leave the unit. The channel may be laterally displaced with respect to an axis shared by the inlet and the outlet.

In this regard, the channel may, for example, be defined by a sump of the unit. Alternatively, the channel may be disposed laterally (e.g. to a side) of the electrode assembly. In a further alternative, the channel may be disposed above the electrode assembly. The electrode assembly may have an electrode plate that is parallel to the axis. Alternatively, the electrode assembly may have an electrode plate that is perpendicular to the axis.

In an embodiment, the channel may be arranged such that some of the water when so flowing through the unit is split between the electrode assembly and the channel.

In an embodiment, the unit may be arranged for the electrode assembly to be removably received therein. The unit may comprise an electrode assembly port arranged for the electrode assembly to be passed therethrough. The electrode assembly port may be arranged to receive a closure that seals the port when so received.

In a second aspect there is disclosed a unit for a salt water pool chlorinator. The unit is arranged for water to flow through the unit. The unit comprises an electrode assembly port in a wall of the unit, so that an electrode assembly may be removably received in the unit via the electrode assembly port. A channel is defined by a wall of the unit and a wall of the electrode assembly when the electrode assembly is received in the unit. The electrode assembly is arranged for some of the water to flow therethrough and the channel is arranged for some other of the water to flow therethrough. The unit further comprises at least one port arranged at the channel. At least one of a sensor, a feeder and/or an extractor is able to use the port to respectively detect, feed into and/or extract water in the channel.

The unit disclosed in the second aspect may be otherwise as defined in the first aspect.

In a third aspect, a unit for a salt water pool chlorinator is disclosed. The unit is arranged for water to flow through the unit. The unit comprises an electrode assembly port in a wall of the unit, so that an electrode assembly may be removably received in the unit via the electrode assembly port. A channel is defined by a wall of the unit and a wall of the electrode assembly when the electrode assembly is received in the unit. The electrode assembly is arranged for some of the water to flow therethrough and the channel is arranged for some other of the water to flow therethrough. The unit further comprises at least one of a sensor, a feeder and/or an extractor located at the channel to respectively detect, feed into and/or extract water in the channel.

The electrode assembly may be secured into the electrode assembly port by various suitable forms of securing mechanisms, including a ¼ turn-type fastening mechanism, a screw-type mechanism, a threaded mechanism, or a bayonet-type fastening mechanism.

The unit disclosed in the third aspect may be otherwise as defined in the first or second aspect.

In a fourth aspect, a method of accessing pool water is disclosed. The method comprises one or more of: detecting, feeding into and/or extracting water in the channel, such as through the at least one port arranged at the channel of an installed unit for a salt water pool chlorinator, as described above in the first, second and third aspects.

In an embodiment, the method comprises the step of installing the unit for a salt water pool chlorinator.

In a fifth aspect, a method of treating pool water flowing through a unit is disclosed. The method comprises subjecting the pool water to electrolysis in one part of the unit, and detecting, feeding into and/or extracting water in another part of the unit.

In an embodiment, the method comprises the use of a salt water pool chlorinator as described above in the first, second and third aspects.

BRIEF DESCRIPTION OF THE DRAWINGS

Notwithstanding any other forms which may fall within the scope of the unit and method as set forth in the Summary, specific embodiments of a unit and method for a salt water pool chlorinator will now be described, by way of example only, with reference to the accompanying Figures in which.

DETAILED DESCRIPTION OF SPECIFIC EMBODIMENTS

Figure 1:
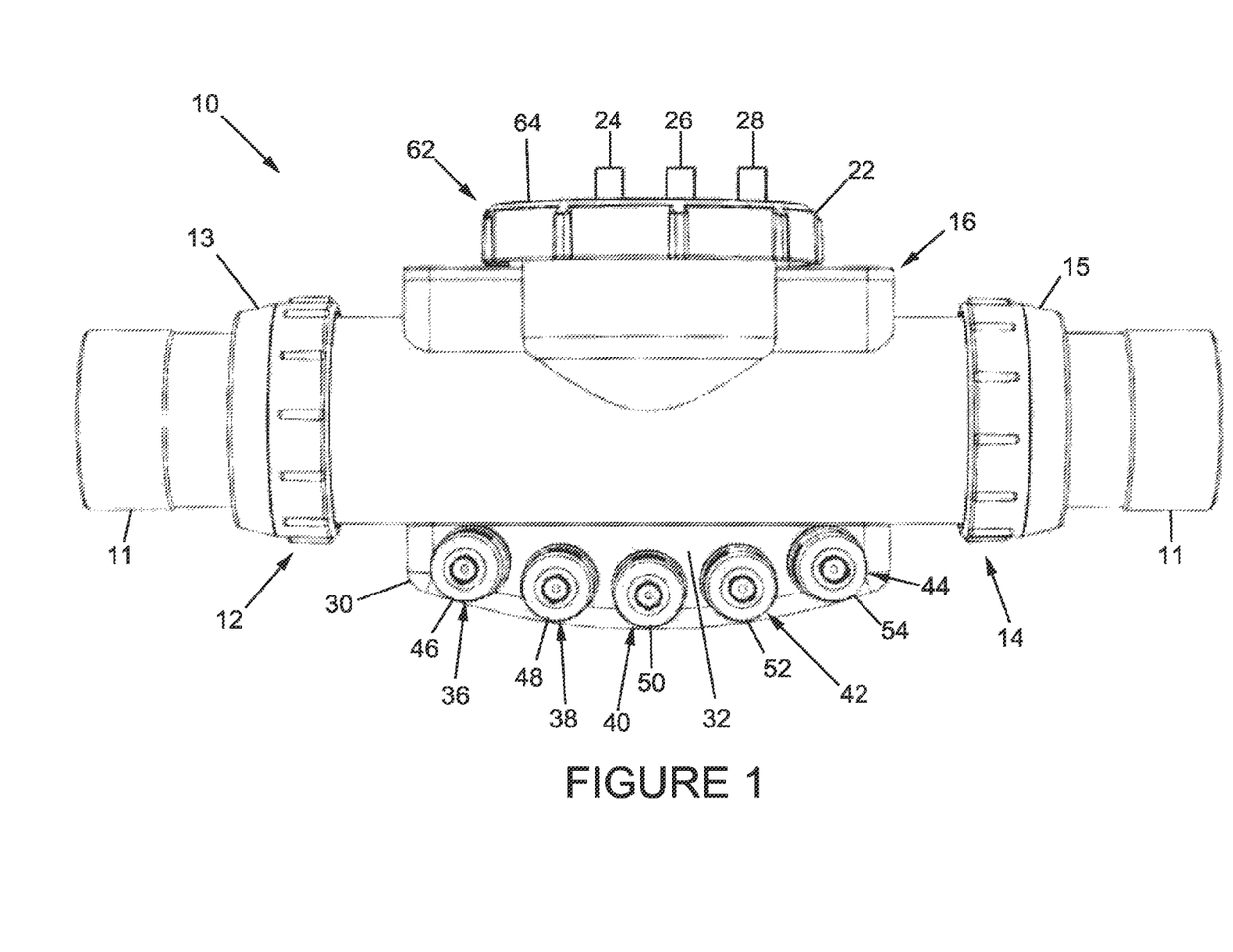
FIG. 1 shows an elevational view of an embodiment of a unit for a salt water pool chlorinator.
Figure 2:
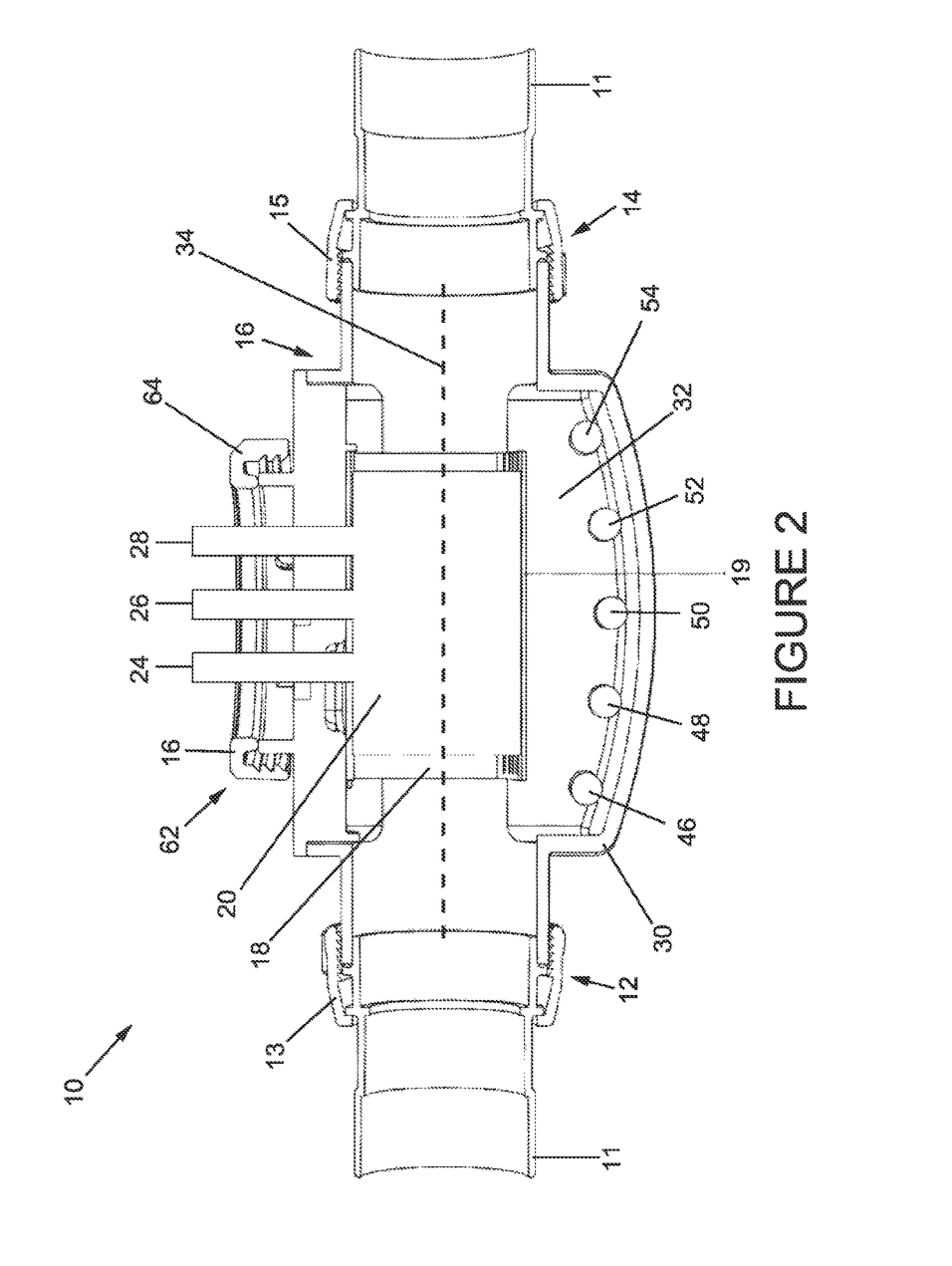
FIG. 2 shows a section view of the embodiment of the salt water pool chlorinator shown in FIG. 1.

FIGS. 1 and 2 show an embodiment of a unit for a salt water pool chlorinator, the unit generally being indicated by the numeral 10. The unit 10 has an inlet 12 for water to enter the unit 10, and an outlet 14 for water to leave the unit 10.

The unit is installed in a pipe 11 that, in use, communicates water from the pool to a pool water pump. The unit is arranged for water to flow through the unit.

The unit 10, in this but not necessarily all embodiments, has an injection moulded housing 16. The housing 16 may be made of any suitable injection moulded polymer including but not limited to epoxy, phenolic, nylon, polystyrene, ABS, polycarbonate and polypropylene. In this embodiment the housing is made of an opaque plastic. The housing may alternatively be transparent. The housing may be any suitable material suitably formed.

The housing 16 has an electrode assembly receptacle 18. The electrode assembly receptacle 18 is arranged for an electrode assembly 20 to be received therein, and has a base 19 which is impermeable to water. In this form the electrode assembly comprises a set of electrode plates, however in other forms the electrode assembly may not be limited to electrode plates and, for example, may further comprise a casing or support structure for the electrode plates.

The electrode assembly receptacle 18 is located between the inlet 12 and the outlet 14 such that some of the water that enters the inlet 12 flows through the receptacle 18 and thus across the conductive plates of the electrode assembly 20. The arrangement of the electrode assembly between the inlet and the outlet defines the configuration of the unit as "in-line".

The electrode assembly when connected to an active electrical source, such as an electrical grid, electrolyses the sodium chloride and/or sodium bromide in the water that enters the inlet 12 and flows across the plates of the electrode assembly 20. The electrolysis generates the sanitizing agents (such as chlorine and/or bromine etc.) in the pool water flowing through the unit. Electrical contacts 24, 26 and 28, for connection with the electrical source, protrude upwardly through a closure 22.

The housing 16 of the unit 10 has a depending portion, in the form of a sump 30. The sump 30, in conjunction with the base 19 of the electrode assembly receptacle 18, defines an internal space which, in this embodiment, is in the form of a channel 32. In this but not necessarily all embodiments, the channel 32 is an extension of the space defined by the housing 16. In other embodiments, however, the channel may be formed by a tube or pipe; one end of the tube being in communication with the water inlet 12, and the other end being in communication with the water outlet 14. In yet another embodiment, the channel may be formed by an internal rebate, groove or gutter located between the inlet 12 and the water outlet 14. Generally, any suitable channel configuration may be used.

The inlet 12 and outlet 14 share an axis 34. In this embodiment, the channel is laterally displaced with respect to the axis 34. In alternative embodiments, however, the channel 32 may be intersected by the axis and it may be the electrode assembly that is laterally displaced with respect to the axis. In yet another embodiment, both the channel and the electrode assembly are laterally displaced with respect to the axis 34.

The electrode plates of the electrode assembly 20 are parallel with the axis 34 so that the water flows freely between the plates with minimal disturbance. In other embodiments, the electrode plates are orientated across the axis 34 and act to disrupt the flow of the water from the inlet 12 to the outlet 14. In yet another embodiment, the plates may be angled to the direction of the water flow. The resulting turbulent flow may improve the electrolysis. Generally, any suitable orientation of the electrode assembly may be used.

The channel 32 is shown, in this embodiment, having a plurality of ports 36, 38, 40 and 44. At port 36 is a sensor 46. In this embodiment, the sensor is in the form of a salt sensor which can detect the concentration of sodium chloride and/or sodium bromide in the pool water flowing through the channel. This and other sensors may be in communication with a processor via a cable or wireless connection, for example. The sensor information generated by the sensor 46 may be received by the processor unit in communication with the sensor 46. The processor unit may process the sensor information and display the concentration (or some indication of the concentration), or use the sensor information to adjust the concentration of the sensed chemical. For example, if the sensor information indicates that the sodium chloride (or sodium bromide) levels are too low, the processor may cause concentrated sodium chloride (or sodium bromide) to be injected through port 38 via a feeder 48.

At port 40 a pH sensor 50 is inserted into the channel 32. The sensor information generated by sensor 50 may be sent to the processor which may process the information. The processor may display an indication of the pH on a display and/or cause a feeder 52 in port 42 to inject at least one of (but not limited to) a buffer, an acid, and an alkaline solution to appropriately adjust the pH.

At port 44 is an extractor 54. Extractor 54 may comprise an inlet, and may be arranged to be attached to a conduit which can take a sample of the water in the channel 32 and deliver it to another place. For example, extractor 54 may be in communication with a remotely located sensor, for example a sensor adjacent or at the processor. Alternatively, the extractor 54 may extract water from the channel 32 and communicate it to a mixer which mixes the extracted water with a chemical and then reintroduces the water into the channel through a feeder as appropriate. Generally, the extractor may be used for any suitable purpose.

Figure 3:
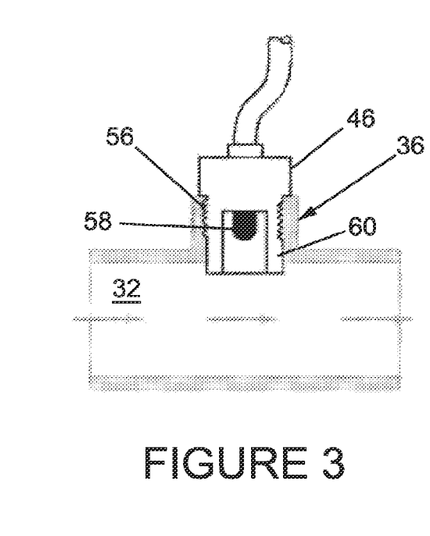
FIGS. 3 to 5 show schematic views of various example sensors at a port of the unit.
Figure 4:
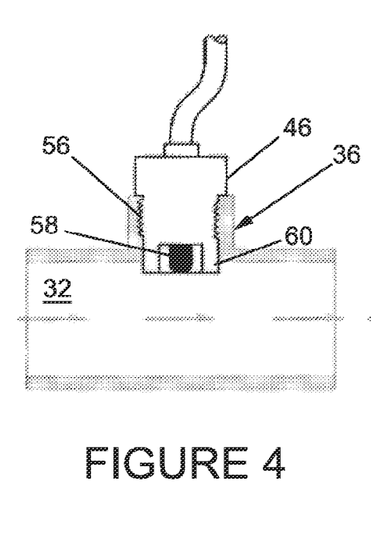
Figure 5:
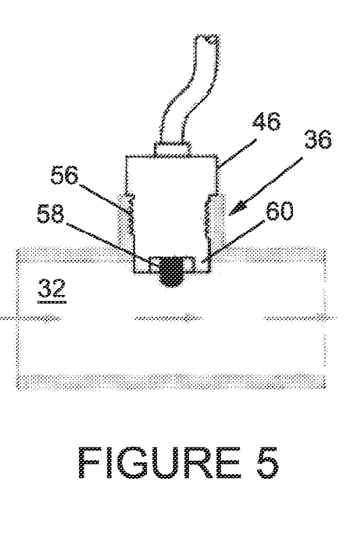

FIGS. 3 to 5 show various configurations of sensors at one of the ports, in this case port 36. The sensor 46 is secured to the port 36 by a screw thread 56. In other embodiments, alternate or additional sensor fastening mechanism may be used such as bayonet fastening, a clip, a screw, an adhesive, or generally any suitable fastening mechanism. Feeders and extractors may be similarly secured. The active sensor tip 58 may be recessed within a cowl 60 of the sensor 46 as shown in FIG. 2. Alternatively, as shown in FIG. 3, the sensor tip 58 may be flush with the opening of the cowl 60. Alternatively, as shown in FIG. 4, the sensor tip 58 may protrude out of the cowl 60 and into the channel 32.

Returning to FIG. 1, the unit 10 is arranged for the electrode assembly 20 to be removably received therein. The unit 10 has an assembly port generally indicated by the numeral 62 which is closed by a closure 64. The closure has a screw thread which can be threaded onto a corresponding thread on a rim of the port. To insert or remove the electrode assembly 20, the closure 64 is screwed off to reveal the open port 62 through which the electrode assembly is passed. Generally, the closure may be any suitable closure and may be alternatively or additionally fastened to the port using any suitable mechanism, such as a ¼ turn configuration, screws, threaded, or bayonet-type configuration. These options for securing the closure are respectively shown in FIGS. 14 to 17. Other suitable fastening mechanisms may also include clips or straps. Costs associated with replacing the electrode assembly or the need for skilled labour may be avoided or reduced. Accordingly, the port may be configured such that an unskilled person may remove and insert the electrode assembly.

The underside of the closure 64 may have attached thereto a gasket in the form of a resilient material, examples of which include but are not limited to rubber and silicone. Alternatively, the gasket need not be attached to the closure and may be in the form of an O-ring seal, for example.

To install the unit 10, a pipe 11 that in use communicates water from the pool to a pool water pump may be cut to expose two pipe ends that are coupled to the unit by collar portions 13 and 15. In other embodiments, flexible tubes may be slipped over the pipe ends and the inlet 12 and outlet 14. Constricting collars or clamps may fasten the tubes to the pipe ends. In other embodiments, the pipe ends may be dimensioned to snugly fit within the inlet and outlet. An adhesive may be applied to the outside surface of the pipe ends which are then inserted to the respective inlet or outlet. Alternatively, the two pipe ends may be dimensioned to fit over the inlet or outlet. Generally, the unit may be installed by any suitable mechanism.

Figure 6:
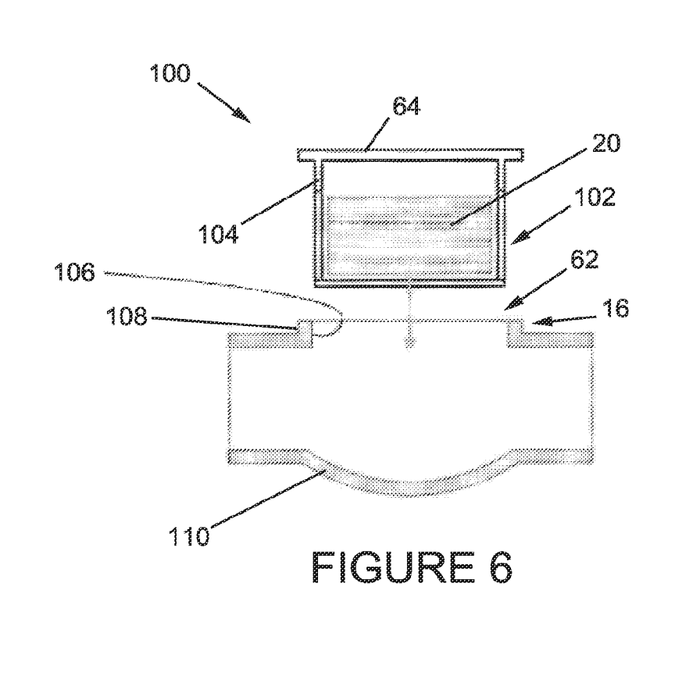
FIG. 6 shows a simplified cross sectional view of another embodiment of a unit for a salt water pool chlorinator with an electrode assembly removed.
Figure 7:
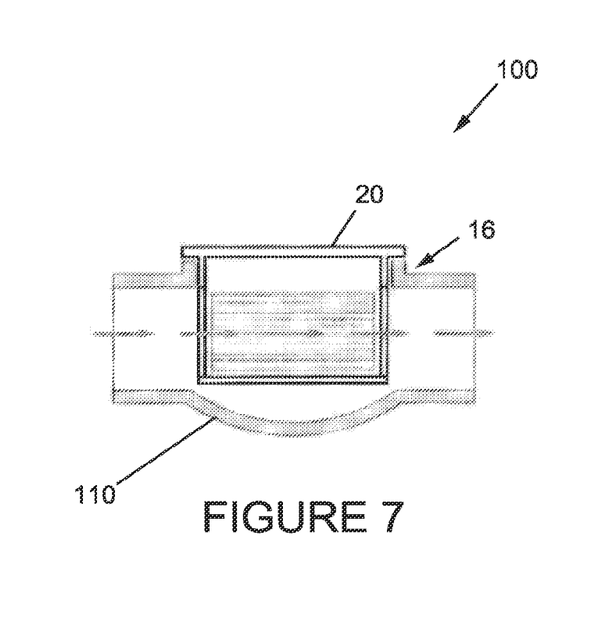
FIG. 7 shows the unit for a salt water pool chlorinator of FIG. 6 but with the electrode assembly received therein.
Figure 8:
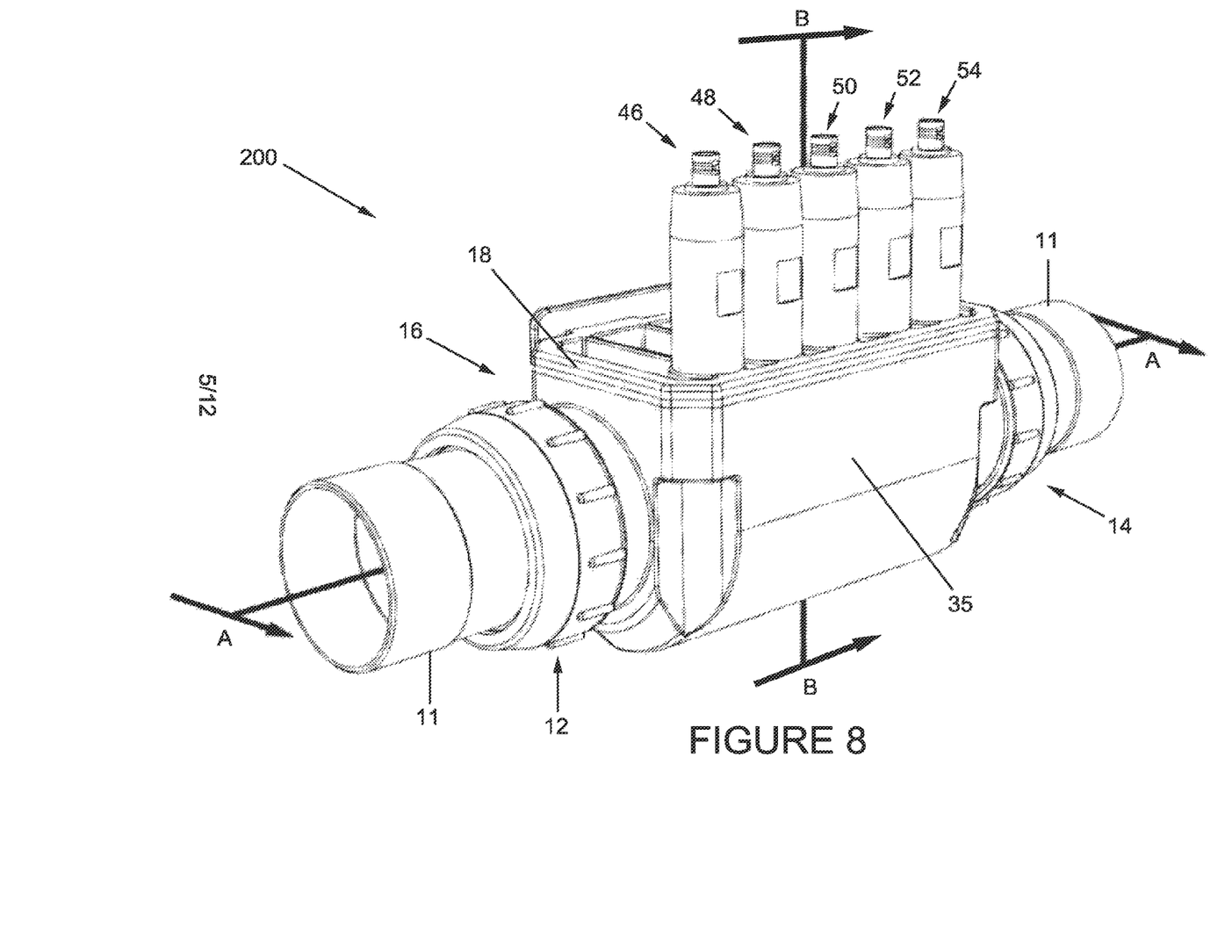
FIG. 8 shows a perspective view of another embodiment of a unit for a salt water pool chlorinator.
Figure 9:
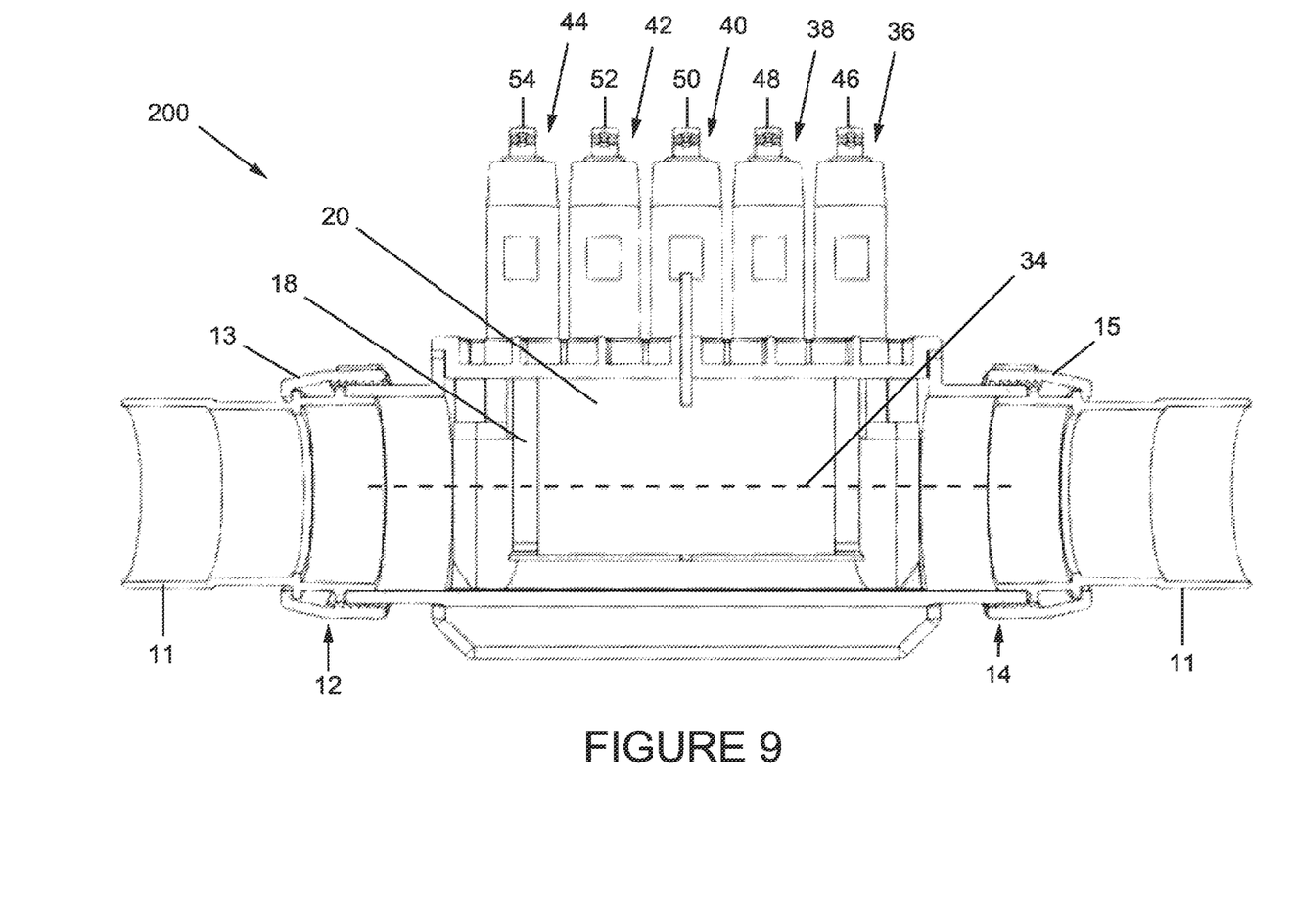
FIG. 9 shows a section view taken on line A-A of the embodiment of the salt water pool chlorinator shown in FIG. 8.
Figure 10:
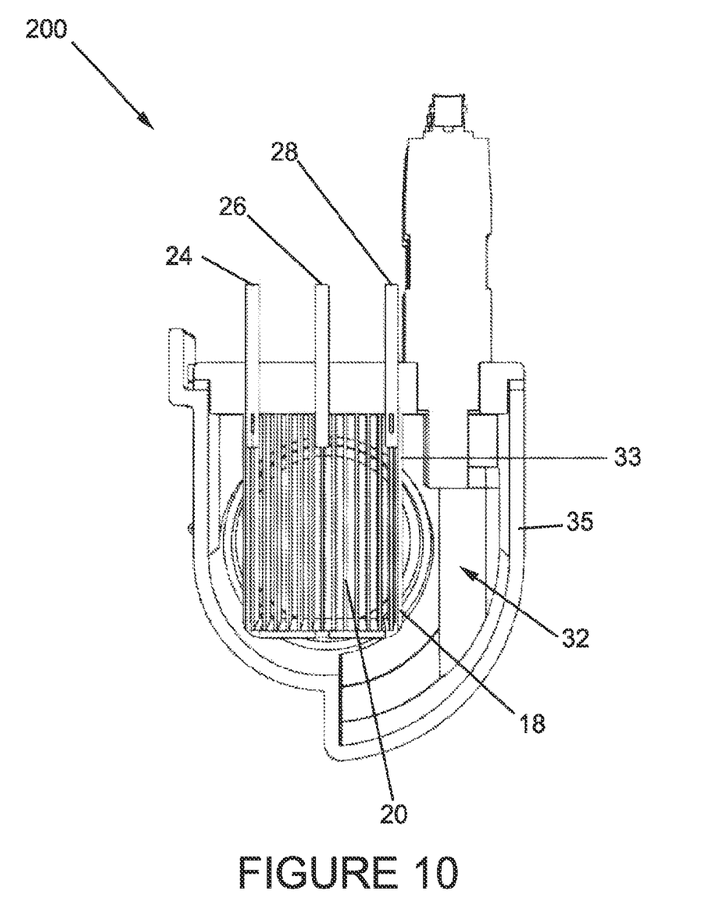
FIG. 10 shows a section view taken on line B-B of the embodiment of the salt water pool chlorinator shown in FIG. 8.
Figure 11:
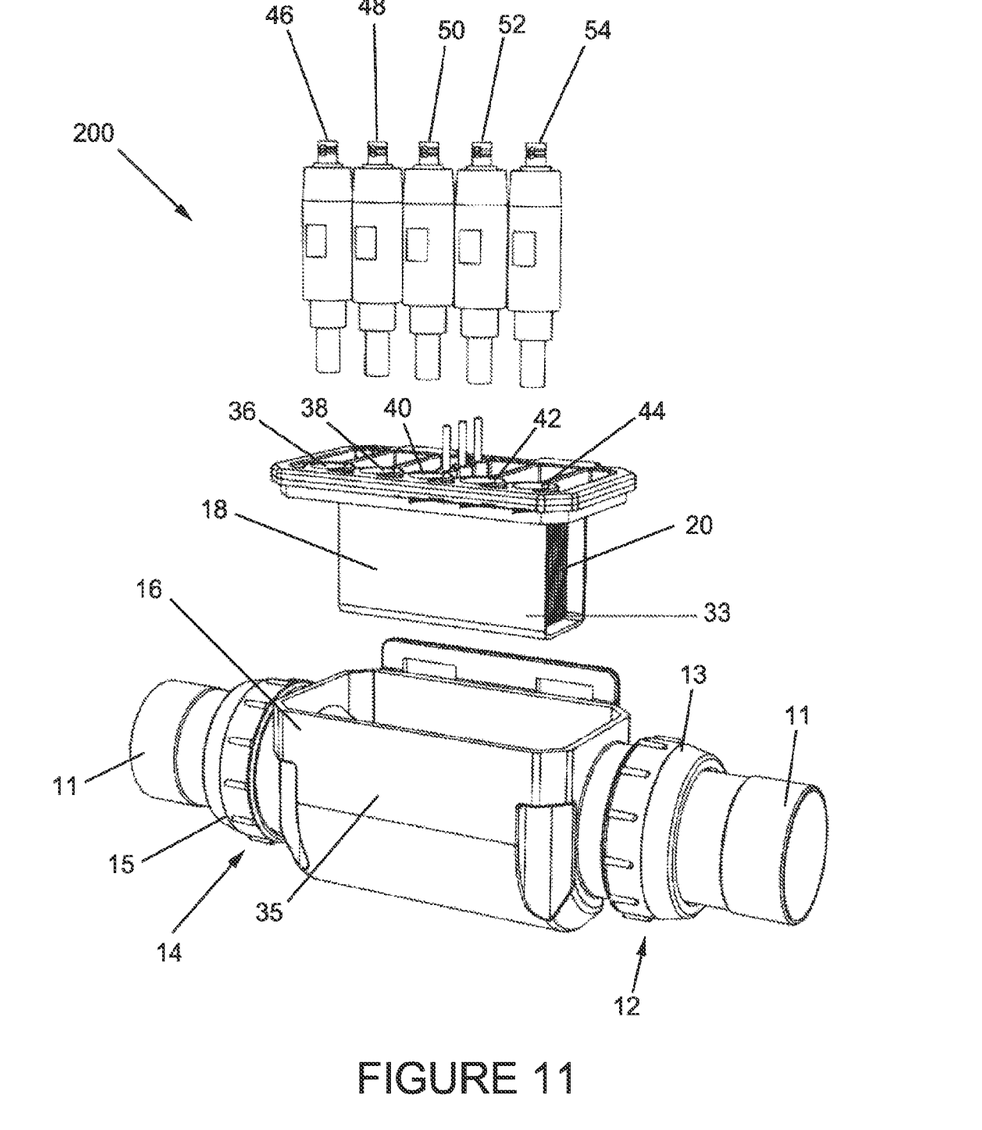
FIG. 11 shows an exploded perspective view of the salt water pool chlorinator of FIG. 8.

FIGS. 6 and 7 show a simplified cross sectional view of another embodiment of a unit 100, wherein parts of similar form and/or function to those in FIG. 1 are similarly numbered. FIG. 6 shows a unit 100 with the electrode assembly 20 removed, whereas FIG. 7 shows the electrode assembly 20 received by the housing 16. In this embodiment, the closure 64 is attached to the electrode assembly 20 to form a cartridge 102. An outward facing surface 104 of the cartridge is threaded and mates with a correspondingly threaded surface 106 at the rim 108 of the assembly port 62. Generally, the cartridge 102 may be coupled to the port using any suitable mechanism as described above. Sensors, feeders and extractors may be coupled to a sump 110.

FIGS. 8 to 11 show various views of another embodiment of a unit for salt water pool chlorinator, the unit being generally indicated by the numeral 200. Parts similar in form or function to those of the embodiment of FIG. 1 are similarly numbered. The electrode assembly 20 has been received by the electrode assembly receptacle 18 of the housing 16 of unit 200. In this embodiment, the channel 32 is defined by a wall 33 of the electrode assembly receptacle 18 and a wall 35 of the housing 16. Furthermore, the channel in this embodiment is not at the bottom, but to one side. Sensors such as 46 and 50 sense properties of water in the channel 32.

Figure 12:
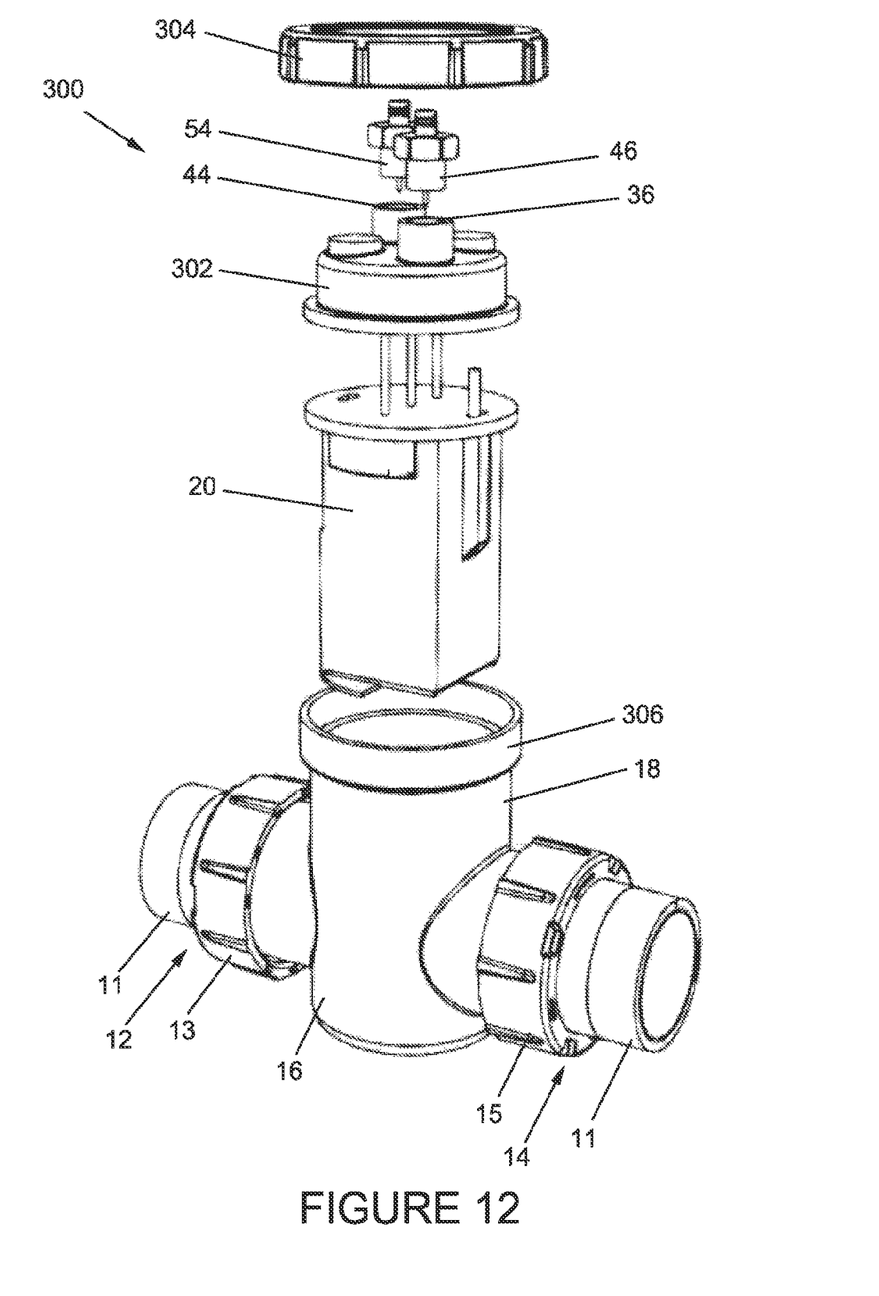
FIG. 12 shows an exploded perspective view of yet another embodiment of a unit for a salt water pool chlorinator.

FIG. 12 shows an exploded perspective view of another embodiment of a unit for a salt water pool chlorinator, the unit being generally indicated by the numeral 300. Parts similar in form or function to those of the embodiment of FIG. 1 are similarly numbered. The electrode assembly 20 is again received in the receptacle 18 of the housing 16 of unit 300. However, in this embodiment, the channel 32 is defined within a cover 302 for the electrode assembly receptacle 18, whereby the channel is able to be located in use above the electrode assembly receptacle. The cover 302 is secured to the receptacle 18 by a collar 304 (e.g. which connects to a rim 306 of the receptacle 18 via a screw—or bayonet-fitting, etc). Thus, the channel lifts out, as such, together with the top-removable/insertable electrode assembly 20. Top-mounted sensors such as 46 and 50, having a squat configuration, again sense properties of water in the channel 32.

Figure 13:
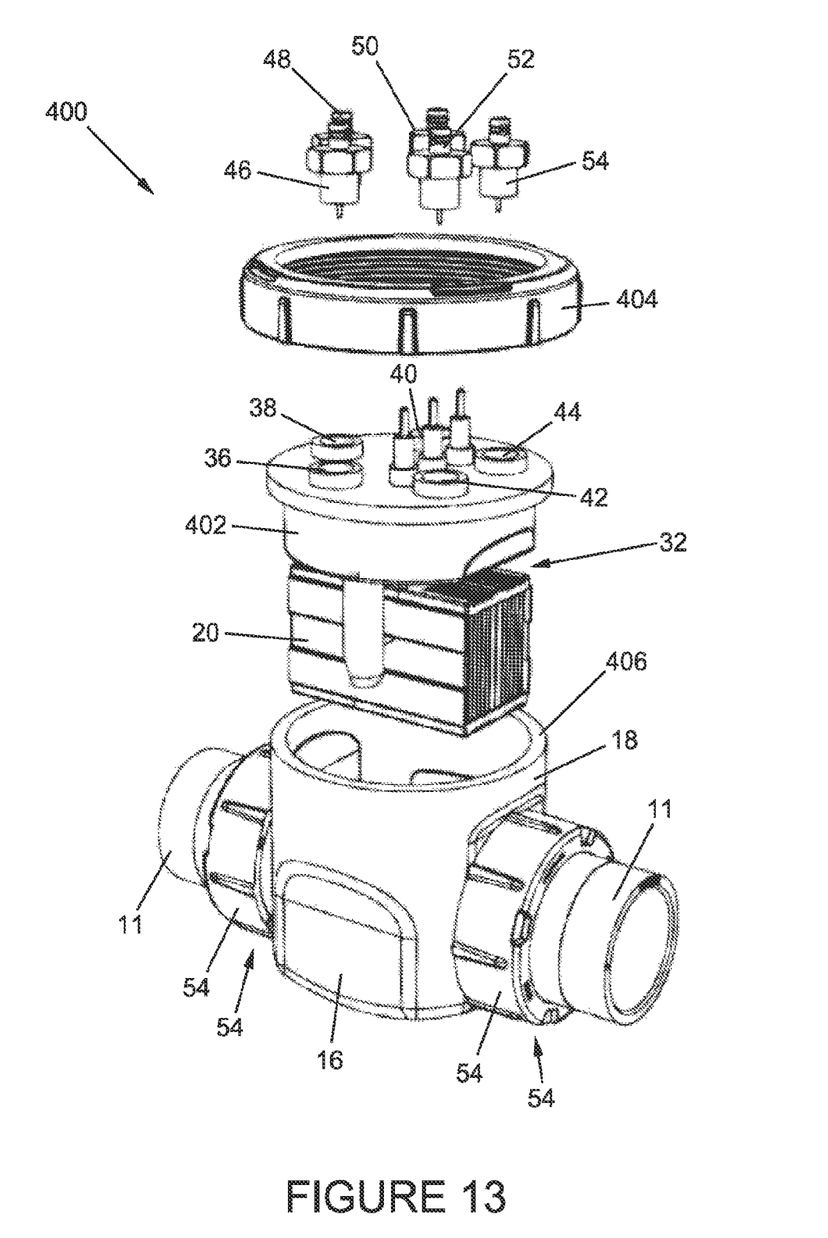
FIG. 13 shows an exploded perspective view of yet a further embodiment of a unit for a salt water pool chlorinator.
Figure 14:
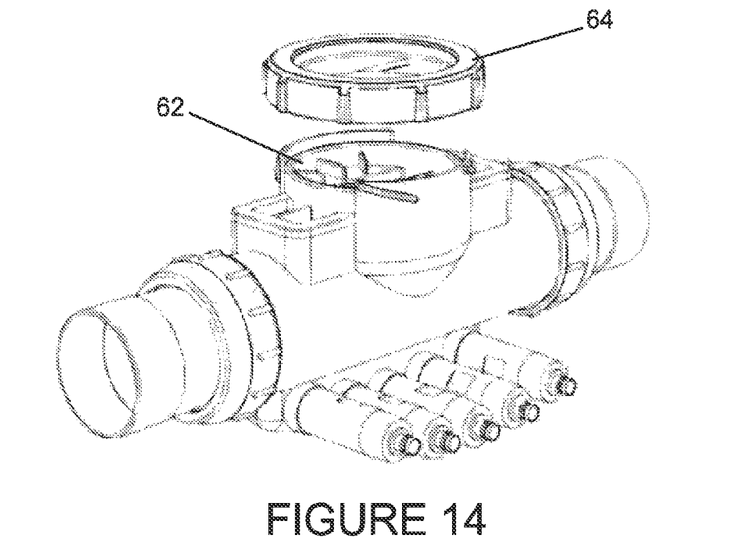
FIG. 14 shows a ¼ turn-type closure.
Figure 15:
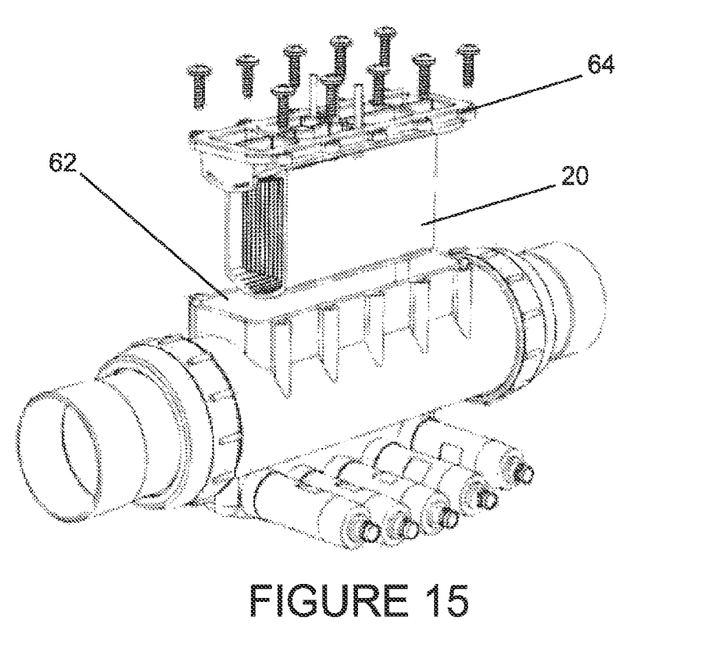
FIG. 15 shows a closure fastened with screws.
Figure 16:
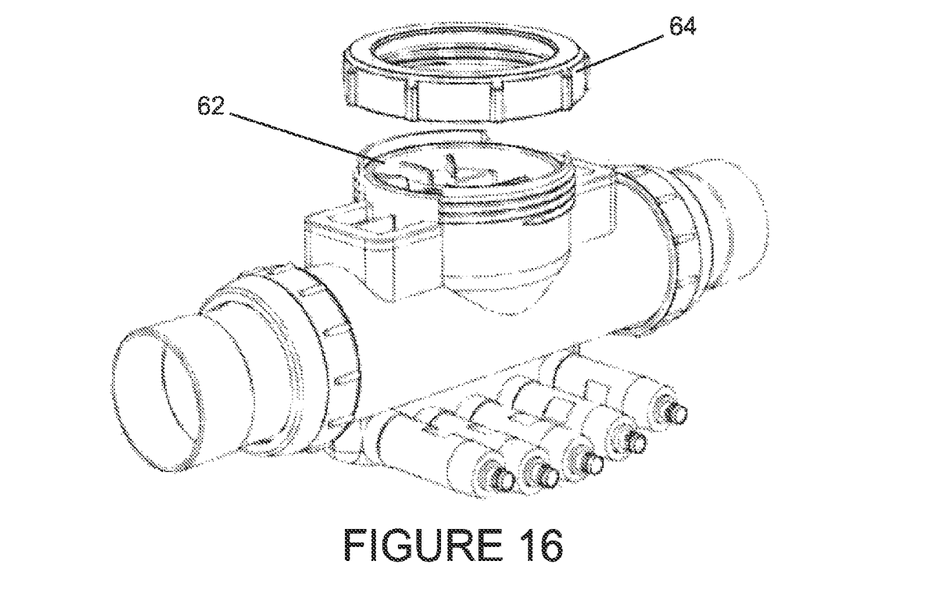
FIG. 16 shows a threaded closure.
Figure 17:
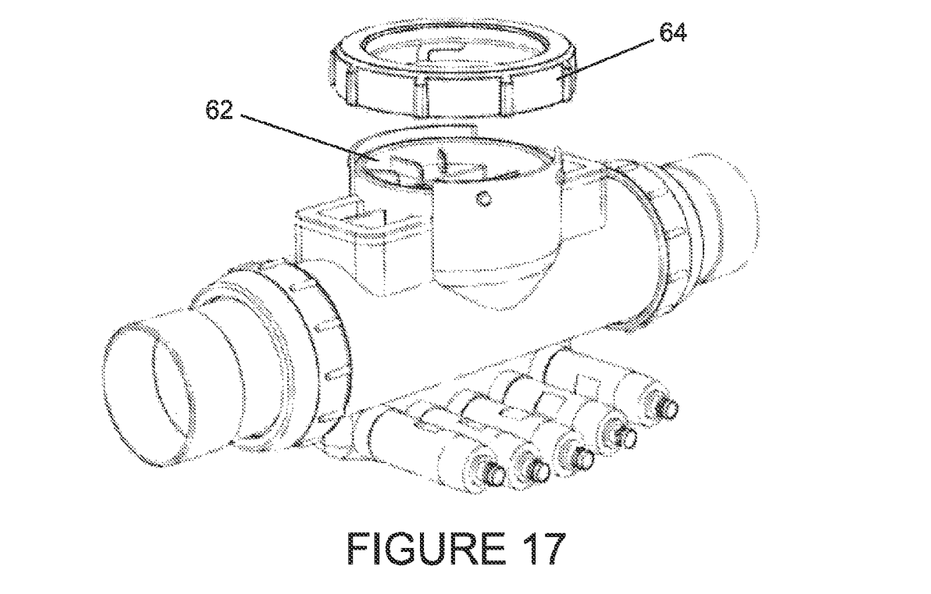
FIG. 17 shows a bayonet-type closure.

FIG. 13 shows an exploded perspective view of yet another embodiment of a unit for salt water pool chlorinator, the unit being generally indicated by the numeral 400. Parts similar in form or function to those of the embodiment of FIG. 1 are similarly numbered. The electrode assembly 20 is again received in the receptacle 18 of the housing 16 of unit 400. Again, in this embodiment, the channel 32 is defined within a cover 402 for the electrode assembly receptacle 18, whereby the channel is able to be located in use above the electrode assembly receptacle. The cover 402 is again secured to the receptacle 18 by a collar 404 (e.g. which connects to a rim 406 of the receptacle 18 via a screw- or bayonet-fitting, etc). Thus, in this embodiment the channel also lifts out together with the top-removable/insertable electrode assembly 20. Top-mounted sensors such as 46 and 50, again having a squat configuration, sense properties of water in the channel 32.

While a number of specific embodiments of a unit and method have been described, it should be appreciated that the unit and method may be embodied in many other forms.

In the claims which follow, and in the preceding description, except where the context requires otherwise due to express language or necessary implication, the word "comprised" in variations such as "comprises" or "comprising" are used in an inclusive sense, i.e. to specify the presence of the stated features but not to preclude presence or addition of further features in various embodiments of the unit and method as disclosed herein.

The invention claimed is:

1. A salt water pool chlorinator, the salt water pool chlorinator comprising:
    an inlet and an outlet through which water flows;
    an electrode assembly positioned in the salt water pool chlorinator such that the electrode assembly intersects a longitudinal axis containing the inlet and the outlet, wherein a first portion of the water flows from the inlet, across the electrode assembly, and out the outlet;
    a channel; and
    at least one port arranged at the channel for use by at least one of a sensor, a feeder and an extractor,
    wherein the first portion of the water flows from the inlet to the outlet without flowing across the at least one port, and
    wherein a second portion of the water flows through the channel across the at least one port and bypasses the electrode assembly when flowing from the inlet to the outlet.

2. The salt water pool chlorinator of claim 1 wherein a barrier defines the channel and at least partially comprises a wall of the electrode assembly when the electrode assembly is received in the salt water pool chlorinator.

3. The salt water pool chlorinator of claim 1 further comprising an electrode assembly receptacle arranged for the electrode assembly to be received therein.

4. The salt water pool chlorinator of claim 3 wherein a barrier defines the channel and at least partially comprises a wall of the electrode assembly receptacle.

5. The salt water pool chlorinator of claim 1 wherein the channel is laterally displaced with respect to an axis shared by the inlet and the outlet.

6. The salt water pool chlorinator of claim 1, wherein the channel is:
    defined by a sump of the salt water pool chlorinator;
    disposed laterally of the electrode assembly; or
    disposed above the electrode assembly.

7. The salt water pool chlorinator of claim 1 wherein the electrode assembly has an electrode plate that is parallel to the longitudinal axis.

8. The salt water pool chlorinator of claim 1 wherein the electrode assembly has an electrode plate that is perpendicular to the longitudinal axis.

9. The salt water pool chlorinator of claim 1 arranged for the electrode assembly to be removably received therein.

10. The salt water pool chlorinator of claim 9 further comprising an electrode assembly port arranged for the electrode assembly to be passed therethrough.

11. The salt water pool chlorinator of claim 10, wherein the electrode assembly port is arranged to receive a closure that seals the electrode assembly port when so received.

12. The salt water pool chlorinator of claim 1, wherein at least a portion of the first portion of the water flows from the inlet, across the electrode assembly, and out the outlet in a linear path that is parallel to the longitudinal axis.

13. A salt water pool chlorinator, the salt water pool chlorinator being arranged for water to flow from an inlet of a pipe, through the salt water pool chlorinator, and out an outlet of the pipe, the salt water pool chlorinator comprising:
an electrode assembly port in a wall of the salt water pool chlorinator, arranged for an electrode assembly to be removably received in the salt water pool chlorinator such that the electrode assembly intersects a longitudinal axis containing the inlet and the outlet of the pipe; and
a channel comprising at least one port for use by at least one of a sensor, a feeder and an extractor,
wherein the electrode assembly is arranged for:
a first portion of the water to flow through the electrode assembly without contacting the at least one port;
at least a portion of the water flows through the electrode assembly in a linear path that is parallel to the longitudinal axis; and
a second portion of the water to flow through the channel without contacting the electrode assembly.

14. A salt water pool chlorinator, the salt water pool chlorinator being arranged for water to flow from an inlet of a pipe, through the salt water pool chlorinator, and out an outlet of the pipe, the salt water pool chlorinator comprising:
an electrode assembly port in a wall of the salt water pool chlorinator, arranged for an electrode assembly to be removably received in the salt water pool chlorinator such that a longitudinal axis of the electrode assembly intersects the inlet and the outlet of the pipe; and
a channel comprising at least one port for use by at least one of a sensor, a feeder, and an extractor,
wherein the electrode assembly is arranged for a first portion of the water to flow through the electrode assembly and the channel is arranged for a second portion of the water to flow through the channel.

15. The salt water pool chlorinator of claim 14 wherein the electrode assembly is secured into the electrode assembly port by a:
1/4 turn-type fastening mechanism;
screw-type mechanism;
a threaded mechanism; or
a bayonet-type fastening mechanism.

16. The salt water pool chlorinator of claim 14, wherein at least a portion of the first portion of the water flows through the electrode assembly without contacting the at least one port in a linear path that is parallel to the longitudinal axis.

17. A method of treating pool water, the method comprising:
moving the pool water through an inlet;
separating the pool water into a first water flow and a second water flow;
moving the first water flow through an electrode assembly received within a first part of a salt water pool chlorinator such that a longitudinal axis of the electrode assembly intersects the inlet and an outlet;
subjecting the first water flow to electrolysis in the first part of the salt water pool chlorinator;
moving the first water flow through the outlet;
moving the second water flow though a channel in a second part of the salt water pool chlorinator to bypass the electrode assembly;
detecting, feeding into or extracting the pool water in the second water flow in the second part of the salt water pool chlorinator; and
moving at least a portion of the second water flow through the outlet.

18. The method of treating pool water of claim 17, wherein the first water flow flows through the electrode assembly when the electrode assembly is received in the the salt water pool chlorinator, the salt water pool chlorinator further comprising:
at least one port arranged at the channel for use by at least one of a sensor, a feeder and an extractor.

19. The method of treating pool water of claim 17, wherein the salt water pool chlorinator further comprises:
an electrode assembly port in a wall of the salt water pool chlorinator, arranged for the electrode assembly to be removably received in the first part of the salt water pool chlorinator,
wherein the first water flow flows through the electrode assembly when the electrode assembly is received in the salt water pool chlorinator, and
wherein the salt water pool chlorinator further comprises at least one port arranged at the channel wherein at least one of a sensor, a feeder and an extractor detects, feeds into, or extracts water in the channel.

20. The method of treating pool water flowing through the salt water pool chlorinator of claim 17, wherein the salt water pool chlorinator further comprises:
an electrode assembly port in a wall of the salt water pool chlorinator, arranged for the electrode assembly to be removably received in the first part of the salt water pool chlorinator,
wherein the first water flow flows through the electrode assembly when the electrode assembly is received in the salt water pool chlorinator and at least a portion of the first water flow flows through the inlet, the electrode assembly, and the outlet in a linear path that is parallel to a longitudinal axis without contacting the channel, and
wherein the salt water pool chlorinator further comprises at least one of a sensor, a feeder or an extractor disposed in the channel to detect, feed into, or extract water.

* * * * *